US010632239B2

(12) United States Patent
Jarvik

(10) Patent No.: US 10,632,239 B2
(45) Date of Patent: Apr. 28, 2020

(54) SINGLE INFLOW DOUBLE SUCTION CENTRIFUGAL BLOOD PUMP

(71) Applicant: Jarvik Heart, Inc., New York, NY (US)

(72) Inventor: Robert Jarvik, New York, NY (US)

(73) Assignee: Jervik Heart, Inc., New York, NY (US)

( * ) Notice: Subject to any disclaimer, the term of this patent is extended or adjusted under 35 U.S.C. 154(b) by 0 days.

(21) Appl. No.: 15/836,409

(22) Filed: Dec. 8, 2017

(65) Prior Publication Data

US 2019/0175804 A1    Jun. 13, 2019

(51) Int. Cl.
*A61M 1/10* (2006.01)
*A61M 1/12* (2006.01)

(52) U.S. Cl.
CPC ........ *A61M 1/1031* (2014.02); *A61M 1/1012* (2014.02); *A61M 1/1017* (2014.02); *A61M 1/1086* (2013.01); *A61M 1/122* (2014.02); *A61M 1/1013* (2014.02); *A61M 2205/3334* (2013.01)

(58) Field of Classification Search
CPC .. A61M 1/1031; A61M 1/122; A61M 1/1086; A61M 1/1013; A61M 1/10; A61M 1/101
See application file for complete search history.

(56) References Cited

U.S. PATENT DOCUMENTS

| 4,688,998 A | 8/1987 | Olsen |
| 5,399,074 A | 3/1995 | Nose et al. |
| 5,824,070 A | 10/1998 | Jarvik |
| 5,938,412 A | 8/1999 | Izraelev |
| 8,088,059 B2 | 1/2012 | Jarvik |
| 9,616,157 B2 | 4/2017 | Akdis |
| 9,835,158 B2 | 12/2017 | Schob |
| 2003/0163019 A1 | 8/2003 | Goldowsky |
| 2011/0008149 A1 | 1/2011 | Jarvik |
| 2012/0253103 A1* | 10/2012 | Robert ................. F04D 29/445 600/16 |
| 2017/0258981 A1 | 9/2017 | Franano et al. |
| 2017/0340788 A1* | 11/2017 | Korakianitis ........... A61M 1/12 |

OTHER PUBLICATIONS

International Search Report and Written Opinion issued in corresponding International Patent Application No. PCT/US18/64608 dated Feb. 22, 2019.

* cited by examiner

*Primary Examiner* — Scott M. Getzow
(74) *Attorney, Agent, or Firm* — Troutman Sanders LLP

(57) ABSTRACT

A centrifugal blood pump uses the "double suction" arrangement of the blood flow channels, by dividing the blood flow across the impeller into two practically identical streams, one flowing across the upstream side of the impeller and the other flowing across the downstream side. The double suction arrangement is obtained by using a "flow through cone bearing" mounted to the hub of the impeller. The impeller is attached to the driving motor by three posts, which do not significantly diminish the flow area. The annular flow through the motor "air gap" reaches the flow channel as a single stream and divides into two streams in the vicinity of the posts. The flow is distributed equally to the two sides of the impeller. After passing across the impeller the two streams combine into one that enters the spiral volute and continues past the pump cutwater and through the outflow channel.

7 Claims, 4 Drawing Sheets

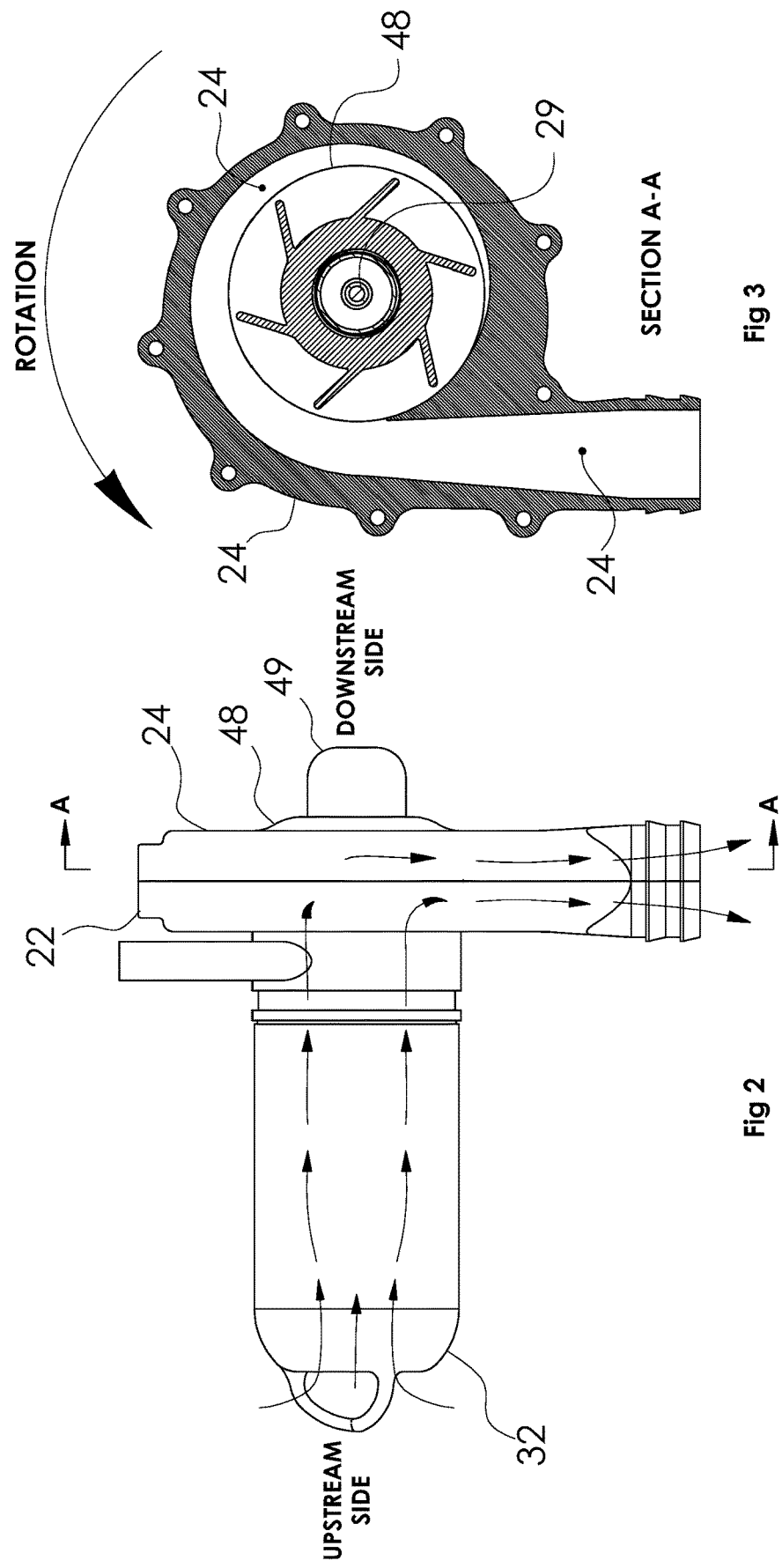

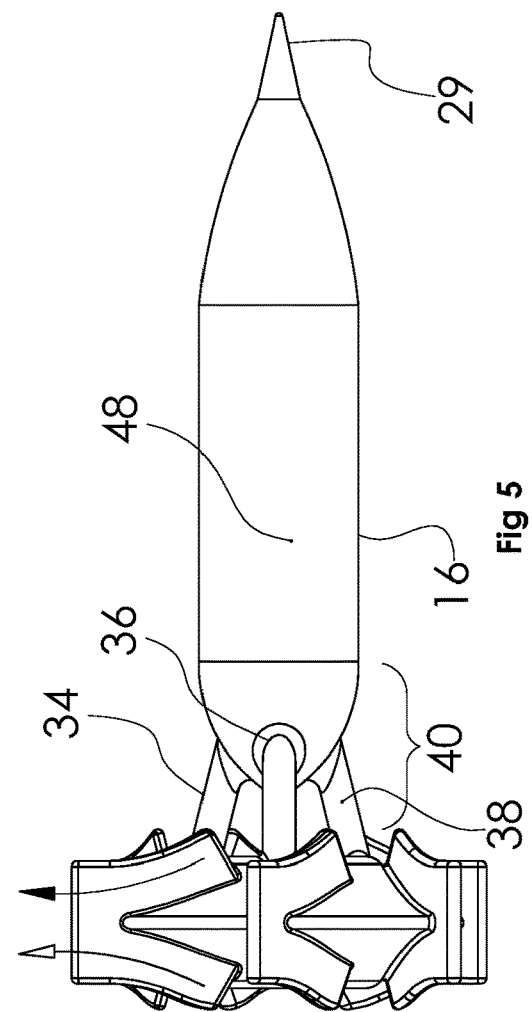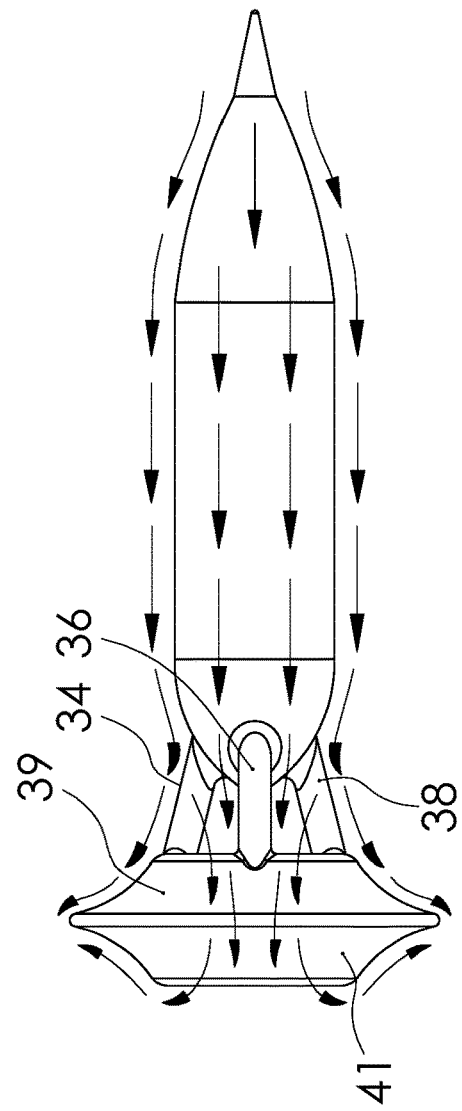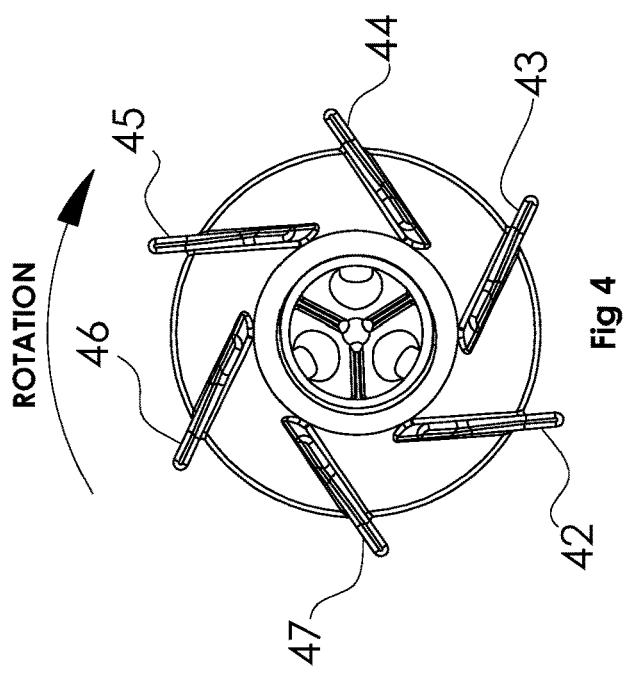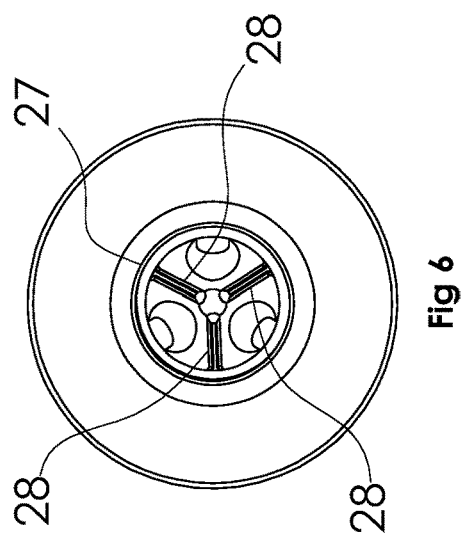
Fig 5
Fig 7
Fig 4
Fig 6

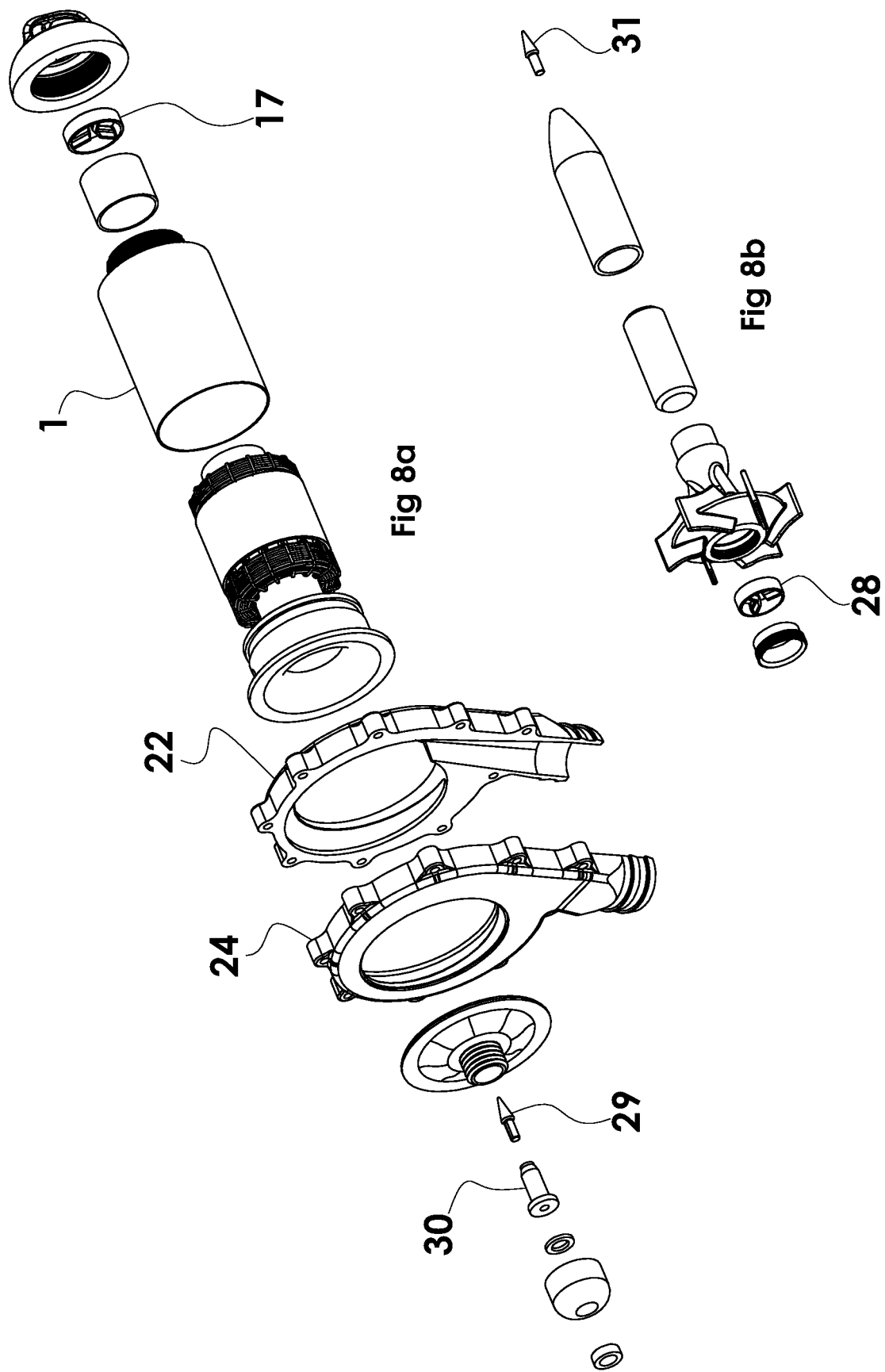

SINGLE INFLOW DOUBLE SUCTION CENTRIFUGAL BLOOD PUMP

FIELD OF THE INVENTION

The present invention is a centrifugal pump using of blood immersed bearings to levitate the pump rotor.

BACKGROUND

The field of mechanical circulatory support has expanded immensely over the last few decades. Survival has reached 10 years for patients implanted with axial flow blood pumps. (example: the Jarvik 2000 and the HeartMate II). In addition to the axial flow models, centrifugal flow rotary blood pumps such as the Heartware and HeartMate3 have been implanted in thousands of patients over the past decade. In the years ahead, many of these patients will reach survival beyond a decade. The available flow and pressure has been sufficient, with modest power requirements low enough that a battery weighing only 1 Kg will power the blood pump for more than 8 hours. Durability of the devices has been excellent using blood immersed ceramic bearing designs. This has all but eliminated the need for shaft seals with the exception of temporary catheter mounted miniature pumps intended to be used up to a few weeks, and in one model implantable LVAD. Several pumps using partial or full magnetic suspension of the impeller have been developed. These include the Heartware and the HeartMate 3.

U.S. Pat. No. 5,399,074 (Kyocera) discloses an extracorporeal bypass pump, one embodiment of which includes channels behind the impeller shroud to allow blood to wash behind the shroud and return to the primary blood flow path.

But despite major advances, some important complications continue to occur in all present VADs. These include, 1) infection, 2) formation of thrombus within the pump, 3) embolic and hemorrhagic strokes, and 4) blood damage.

Olsen et al. U.S. Pat. No. 4,688,998 (FIGS. 10 and 11) discloses double suction centrifugal blood pumps but the design requires two inflow conduits. This makes several prior art designs that use them unsuitable because they are too large to implant within the pericardium. U.S. Pat. No. 5,938,412 discloses another example of a double suction blood pump configuration. In this case there is one inflow and two outflow conduits exiting the housing.

U.S. Pat. No. 9,835,158 discloses a centrifugal pump having two "back to back" rotors constituting a double suction design with a bifurcated inflow tube. In the embodiment shown in FIG. 1, the bifurcation requires a large housing to accommodate duel inflow tubes downstream of the bifurcation that pass through the motor. This results in a complex pump that is too large to implant in the apex of the left ventricle and requires an abdominal pump pocket to fit it in the body. The same is true of the other embodiments that utilize motor and magnetic levitation windings surrounding the pump impellers. In the embodiment shown in the '158 patent, FIG. 3, a blood inflow tube with side holes passes through the magnetically levitated rotor, thereby supplying blood to the inflow of both "back to back" impellers. But the use of side holes can cause hemolysis, and they should be avoided where possible. The single inlet double suction design of the present invention allows the blade shape and flow channel to be nearly identical for both sides of the impeller. Without using side holes for the flow or a bifurcated inflow tube the flow is divided into two streams, with approximately 50% passing across each face of the impeller, and the flow re-forms a single stream as the flow enters the volute.

SUMMARY

The present invention addresses all of the above mentioned issues. A radial flow impeller is used because present data show that centrifugal pumps produce less blood damage than axial flow pumps and are more energy efficient. Formation of thrombus is prevented by continual washing of all blood contacting surfaces, and the administration of anticoagulants. Bleeding complications may occur because the shear force on the blood is too high and not only breaks blood cells, but breaks the long chain structure of clotting Factor 10, thus blocking the coagulation cascade, and sometimes causing GI bleeding.

The avoidance of infection is accomplished using a percutaneous power cable tunneled from the heart in the chest, under the skin of the neck and through the scalp skin using fixation to the skull to protect the exit site from trauma due to inadvertent tension on the cable (U.S. Pat. No. 5,904,646 infection resistant power cable system for medically implanted electric motors).

The present invention employs a double suction centrifugal or mixed flow pump. Double suction pumps are widely used, in the pump industry because they have virtually no axial hydraulic thrust, due to the back-to-back double suction impeller design. Use of the double suction principle in the present invention yields a device that meets all of the objectives listed above.

A more important characteristic of double suction centrifugal pumps is the ability to function in a design configuration that has no secondary flow path. Backflow through secondary flow channels constitutes leakage flow paths that increase the transit time for blood to pass through a pump. This can be completely avoided by using a shroud-less design. This eliminates narrow low flow channels that are susceptible to blood damage and the formation of thrombus. Red blood cells that rupture under shear stress release hemoglobin into the blood called hemolysis. Blood cells that are exposed to high shear very briefly can withstand much higher shear values than cells with a longer time exposed to high shear. Therefore, pumps that are free of low flow or stagnation zones such as narrow leakage path channels have the advantage of producing less blood damage. Additionally, elimination of low flow leakage channels reduces complications of blood clots, which may occur where blood flow washing is not sufficient. Leakage flow channels, which are predilection sites for thrombus, are completely avoided in the present invention.

The present invention is differentiated from many prior art centrifugal pump patents because it is not magnetically levitated. Use of blood immersed bearings greatly simplifies the design. We have utilized blood immersed bearings for patient support up to 10 years. The use of designs where the blood flows through the center of the motor stator and around the central motor magnet (referred to as the motor "air gap") has been proven reliable in several different VADs used clinically. This permits the blood pump motor housing to serve the function of an inflow cannula as well as the pump motor housing. In the present invention, the radius of the pump volute casing is only a few millimeters larger than the radius of the motor, and the pump is smaller and lighter weight than the HeartMate 3.

The device of the present invention is a combination of the Jarvik 2000 motor and housing, (without axial flow impeller blades), and a double suction centrifugal pump. The invention uses cone bearings having three centrally extending struts that support a ceramic cone on the shaft of the rotor. One bearing set is mounted at the inlet opening of the housing, with the struts stationary and the ceramic cone rotating. The other bearing set is mounted centrally within the impeller hub with its three support struts rotating and the ceramic cone stationary. This is an optimal bearing design because the bearing struts only block a small proportion of the flow area.

1. It is an object of the present invention to provide long term implantable blood pumps capable of operating for greater than ten years with fewer serious adverse events than has been accomplished to date.

2. It is a further object of the invention to provide electrically powered blood pumps that have no predilection sites for thrombus formation and therefore reduce pump thrombus and serious stroke to below 0.005 events per patient year of support.

3. It is another object of the invention to incorporate blood lubricated cone bearings operating at the lowest practical rotational rates (RPM) to avoid blood damage and wear.

4. Another object of the invention is to provide high flow washing across all blood contacting surfaces by eliminating stagnant areas of recirculation and long narrow blood channels.

5. A still further object of the invention is to provide an anatomically stable pump interface by securing it at the apex of the left ventricle with intraventricular placement of the motor and with implant of the pump volute housing outside the apex and within the thorax.

6. An additional object of the invention is to create a space efficient single inlet, double suction, single outflow pump flow geometry, without requiring two inflow conduits formed by a bifurcation of a tubular inflow conduit.

7. An additional object of the present invention is to provide higher energy efficiency and longer battery life than presently available with axial flow pump ventricular assist devices.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 2 is a plain view of the motor housing, volute casing, and outflow tube.

FIG. 3 is a cross sectional view of pump volute and impeller taken along section A-A of FIG. 2.

FIG. 4 is an end view of the rotor and impeller with the blades included.

FIG. 5 is a plain side view of the rotor showing the inflow bearing cone.

FIG. 6 is an end view of the rotor without impeller blades showing the struts of the outflow bearing and the three posts that interconnect the motor rotor hub with the impeller hub.

FIG. 7 is an end view of a bladeless rotor with arrows showing the flow washing across the entire surface of the rotor FIG. 8*a* is an exploded view of the stationary parts of the pump assembly, excluding the rotor parts.

FIG. 8*b* is an exploded view of the rotating parts.

DETAILED DESCRIPTION

Figure 1:
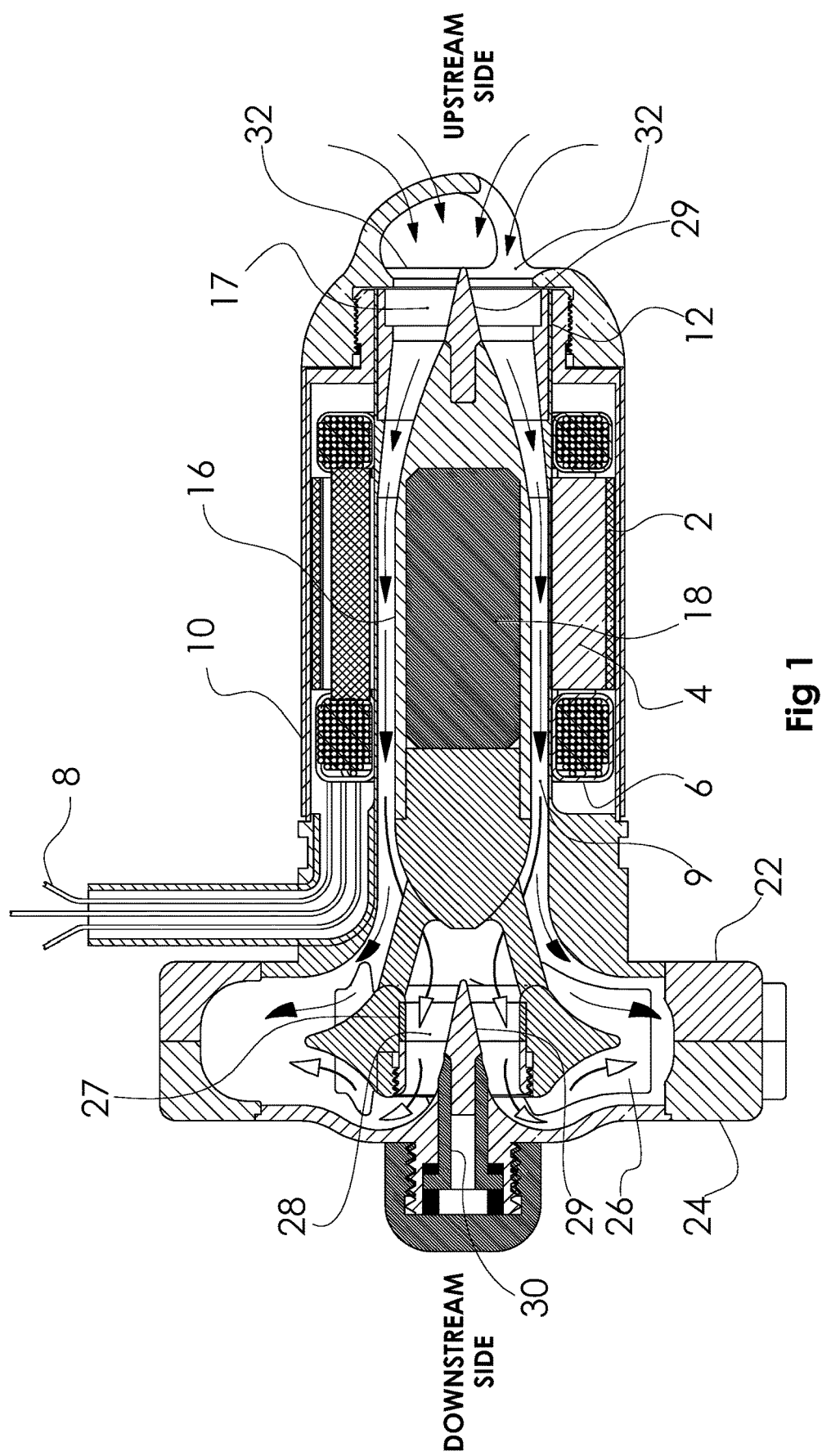
FIG. 1 is a longitudinal section of the pump showing the path of flow (arrows) through the motor, and across the impeller blades on the downstream side of the impeller (black arrowheads, and through the impeller bearing, and across the impeller blades on the upstream side of the impeller (white arrowheads).

Referring to FIGS. 1-8*b*, which illustrate an example of the present invention, an elongated motor stator 2, is located within an inflow conduit and is designed to be inserted into the left ventricular apex. The motor stator is comprised of laminations 4, and windings 6 and has insulated wires 8 exiting the motor housing 10. The stator 2 surrounds the motor bore 9. The pump motor housing supports the ring 12 and posts 14 of an upstream cone bearing 15 (U.S. Pat. No. 8,088,059) and is joined to a centrifugal pump volute with the volute outside the heart near the apex. This is the configuration shown in U.S. Pat. No. 5,824,070, titled Hybrid flow blood pump.

By convention we define the upstream side of the pump, as the inflow side of the device, and define the downstream side as the outflow side of the pump (labeled in FIGS. 1 & 2).

A motor rotor 16 that contains the motor magnet 18 is supported on one end by the upstream cone bearing struts 17. The motor rotor is affixed to a centrifugal impeller 26 located within the split volute housing 22, 24. The impeller centrally mounts the ring 27 and struts 28 of a flow through cone bearing. The small bearing cone 29 is mounted on a stationary post 30 centrally aligned with the long axis of the motor rotor. The upstream bearing struts 17 are stationary. The upstream bearing cone 31 is mounted on the axis of rotation of the rotor 16 at the upstream end of the rotor 16, whereas the downstream bearing cone 29 is stationary, and the downstream bearing struts rotate with the impeller. The outside diameter of the motor housing may be approximately 25 mm or less. The volute housing may be approximately 50 mm diameter by 15 mm thick.

Blood enters the upstream opening 32 in the motor housing and 100% of the flow passes through the upstream bearing 17. Near the downstream end of the motor housing the motor rotor is attached to the impeller by 3 rotating support posts 34, 36, 38 (see FIGS. 2 & 5) allowing unrestricted flow through the downstream bearing. The flow becomes divided as it flows past the rotor support posts with about 50% flowing through the downstream bearing and then across the downstream face of the impeller hub 39 and between impeller blades 42, 43, 44, 45, 46, 47, and the other 50% flowing across the upstream face of the impeller hub 41 and impeller blades. This is shown in FIG. 1 by the solid black arrowheads representing flow through the motor, past the rotor support posts and across the upstream side of the impeller. The white arrowheads represent the flow that passes through the downstream cone bearing, and then across the downstream face of the impeller hub. After passing across the impeller blades, both streams merge and circumferentially flow into the volute housing 22, 24. Thus the structure forms a double suction hydrodynamic pump with only a single inflow conduit, in an overall configuration well suited to anatomic positioning at the apex. FIG. 7 shows that the flow (arrows) washes the entire surface of the rotor and illustrates blood flowing through the outflow bearing Double suction centrifugal pumps are a widely used pump type, with advantages when used in a blood pump. They have virtually no axial hydraulic thrust, due to the back-to-back/double suction impeller design. A more important characteristic of double suction centrifugal pumps is the ability to function in a design configuration that has no secondary flow path. Backflow through secondary flow channels constitute leakage flow paths that increase the transit time for blood to pass through a pump, can be completely avoided by using a shroud-less design. This eliminates narrow long flow channels that are susceptible to blood damage and the formation of thrombus. Red blood cells that rupture under shear stress release hemoglobin into the blood called hemolysis. Blood cells that are exposed to high shear very briefly can withstand much higher shear values than cells with a longer exposure, without hemolysis. Therefore, pumps that are free of low flow or stagnation zones have an advantage.

The single inlet double suction design of the present invention allows the blade shape and flow channel to be nearly identical for both sides of the impeller. This causes the flow to be divided into two streams, with approximately 50% passing across each face of the impeller, and then re-form a single stream as the flow enters the volute.

Referring to FIG. 5, the pump rotor is comprised of the motor rotor 18 containing the motor magnet 16, and two tapered ends, one end carrying the bearing cone 29 and the other end carrying the three rotor support posts 34,36, 38. These three posts connect the motor rotor to the hub of the pump impeller. After assembly laser welding can be used to lock the components of the rotor in place, using a holding fixture. All surfaces of the complete pump rotor assembly are then polished to a mirror finish.

The descriptions contained herein are examples of embodiments of the invention and are not intended in any way to limit the scope of the invention. As described herein, the invention contemplates many variations and modifications of the inventive single inlet double suction centrifugal blood pump, including numerous configurations, properties and methods for making the same. Also, there are many possible variations in the materials and configurations of the bearings and rotors. These modifications would be apparent to those having ordinary skill in the art to which this invention relates and are intended to be within the scope of the claims which follow.

What is claimed is:

1. A permanently implantable electrically powered ventricular assist blood pump comprising:
    an electric motor comprising a blood flow channel through the motor air gap;
    a rotor and impeller rotationally supported on mechanical blood immersed upstream and downstream bearings being driven by the electric motor, wherein the rotor is attached to the impeller by rotating support posts;
    a double suction configuration defined as a structure having at least two centrifugal or mixed flow blood pump blades on an upstream side and a downstream side of an impeller hub, such that after passing through the rotating support posts, the flow is divided into an upstream flow and a downstream flow, wherein the pressure and the amount of flow for the upstream flow are approximately equal to the downstream flow;
    a single inlet flow channel directed toward the rotor and the impeller; and
    a single outlet flow channel discharging the blood at the downstream side of the double suction pump configuration.

2. The pump of claim 1, wherein the impeller comprises shroudless impeller blades.

3. The pump of claim 1, wherein:
    the downstream flow further travels through the downstream bearing and across a downstream face of the impeller hub and the blades; and
    the upstream flow further travels across an upstream face of the impeller hub and the blades.

4. The pump of claim 3, wherein after the upstream flow and the downstream flow passes the blades, the upstream flow and the downstream flow merge together.

5. A thrombo-resistant permanently implantable blood pump comprising:
    a streamlined generally cylindrical motor rotor comprising:
        a magnetic core,
        a plurality of support struts affixing the magnetic core co-axially to at least one of
        a centrifugal and mixed flow pump impeller, and
        a gap between the motor rotor and an impeller hub of the impeller;
    a rotating flow through bearing mounted centrally within the impeller hub;
    a plurality of upstream impeller blades on an upstream side of the impeller hub;
    a plurality of downstream impeller blades on a downstream side of the impeller hub;
    a housing with a volute surrounding the upstream and the downstream impeller blades, wherein the housing comprises a contour closely matching a shape of the upstream and the downstream impeller blades such that the gap between the upstream and the downstream impeller blades and the housing is small enough to prevent leakage and large enough to avoid shear that would result in blood damage; and
    a motor armature mounted in a motor housing surrounding the magnetic core of the rotor and supporting an upstream bearing approximately twice a cross sectional area of a flow path of the downstream bearing;
    wherein the flow path divides the total flow into two approximately equal streams, one stream flowing across the upstream side of the impeller, and the second stream flowing through the bearing mounted on the impeller and then across the downstream side of the impeller to create the geometry of a double suction pump.

6. The pump of claim 5, wherein the gap is approximately 0.5 mm to 1.5 mm.

7. A non-thrombogenetic blood pump comprising:
    a cylindrical motor stator enclosed in a generally cylindrical housing;
    an elongated streamlined first rotor containing motor magnets;
    a pair of mechanical blood immersed flow-through bearings supporting the first rotor, comprising:
        an axis of rotation co-axial with the center of a long axis of the housing, and a rotating part of the flow-through bearings mounted on an upstream end of the rotor; and
        a bore of the stator housing substantially larger than a diameter of the first rotor supported inside the motor stator, such that the full flow of the pump passes through the upstream bearing, around the first rotor, and across a downstream end of the first rotor;

an impeller comprising:
- a generally disc shaped hub mounted on the downstream end of the first rotor by a plurality of struts, and
- a plurality of at least two impeller mixed flow or centrifugal flow blades mounted on opposite sides of the hub;

wherein said downstream flow through a downstream bearing mounted centrally within the pump impeller, is supported by a stationary bearing member mounted to the pump housing by a stationary post; and a spiral volute and impeller housing within which the impeller rotates, comprising a portion of the housing through which all of the pump flow passes after being divided into two streams of generally equal flow, one on either side of the rotor hub, and then rejoined into a single stream that exits the pump via the outflow conduit.

\* \* \* \* \*